United States Patent [19]
Emodi et al.

[11] 3,969,524
[45] July 13, 1976

[54] STABLE AMOXICILLIN DOSAGE FORM

[75] Inventors: Alexander S. Emodi, West Orange; Harold Leon Newmark, Maplewood; Leonard Joseph Scialpi, Parsippany, all of N.J.

[73] Assignee: Hoffmann-La Roche Inc., Nutley, N.J.

[22] Filed: Aug. 13, 1974

[21] Appl. No.: 497,158

[52] U.S. Cl. ............................................. 424/271
[51] Int. Cl.$^2$ ....................................... H61K 31/43
[58] Field of Search ................................ 424/271

[56] References Cited
UNITED STATES PATENTS 3,674,776   7/1972   Lowg et al. ..................... 424/271

FOREIGN PATENTS OR APPLICATIONS 2,035,118   12/1970   France .............................. 424/271

*Primary Examiner*—Jerome D. Goldberg
*Attorney, Agent, or Firm*—Samuel L. Welt; Bernard S. Leon; Gerald S. Rosen

[57] ABSTRACT

The preparation of relatively stable injectable solutions from dry powder formulations containing from 1.0 to 2.0 moles of anhydrous sodium carbonate per mole of amoxicillin free acid is disclosed. The solutions are suitable for administration by intravenous and intramuscular injection and intravenous drip.

6 Claims, No Drawings

STABLE AMOXICILLIN DOSAGE FORM

DESCRIPTION OF THE INVENTION

Amoxicillin, D-(-)-alpha-amino-parahydroxybenzyl penicillin, is a semisynthetic penicillin produced in accordance with the processes disclosed in U.S. Pat. No. 3,674,776. Its salts are also known. The compound is readily formulated into stable oral dosage forms and is useful as such to treat bacterial infections. There are instances, however, when an injectable formulation is desired to be used.

In order to form satisfactory injectable solutions of closely related semisynthetic penicillins, e.g., ampicillin, the usual method is to dissolve the sodium salt of the compound in the sterile water for injection and administer within an hour. For administration by intravenous drip, the sodium salt is dissolved in isotonic sodium chloride, 5% dextrose in 0.4% sodium chloride solution, 10% invert sugar in water or a sodium lactate solution and administered as a very dilute, e.g., 0.2%, solution of ampicillin.

These known methods of producing injectable solutions are not suitable for amoxicillin since the sodium salt of amoxicillin is prepared at a pH of about 9 and amoxicillin is very unstable at such high pH's. In fact, amoxicillin is most stable at pH 7 but is relatively unsoluble at that pH.

It has been found that suitable injectable solutions of amoxicillin can be made by forming a stable dry powder mixture of amoxicillin trihydrate and anhydrous sodium carbonate and then dissolving the mixture in the aqueous media for injection, thus forming, in situ, the sodium salt.

It has been found that in order to produce acceptably stable solutions containing, on a weight basis, a sufficient amount of amoxicillin trihydrate to result in about 5, 10 or 20% amoxicillin, it is necessary to take a mixture containing from 1.0 to 2.0 moles of anhydrous sodium carbonate per mole of amoxicillin free acid and dissolve it in the appropriate amount of water. A preferred molar ratio is 1.38–1.75 to one with 1.6 to one most preferred.

The stability criteria for a suitable penicillin intravenous or intramuscular solution is that the active compound must be sufficiently soluble and compatible with the aqueous vehicle utilized in the concentrations required. The vehicle most suitable for intramuscular and intravenous injection in conjunction with the powder compositions of this invention is sterile water. For use in intravenous drip administration, normal saline or a 5% aqueous dextrose solution are suitable. In the intravenous drip formulations the more dilute the formulation, the more stable. Thus, the most suitable concentration of amoxicillin for intravenous drip formulations is about 0.2 to 3% by weight.

For direct intramuscular (IM) or intravenous (IV) injections higher concentrations, though less stable, are suitable because the IM and IV are used immediately after preparation of the solution. Thus, about 5, 10 and 20% concentrations of amoxicillin can be used in the injectable formulations of this invention.

The injectable solutions of this invention are made by blending the appropriate amounts of amoxicillin trihydrate and anhydrous sodium carbonate and adding the amount of vehicle needed to result in the desired concentration.

Alternatively, the anhydrous sodium carbonate can be dissolved in the vehicle which is then added to amoxicillin powder.

When making the intravenous drip solutions, amoxicillin trihydrate and anhydrous sodium carbonate are blended, then sufficient sterile distilled water is added to form a concentrated solution equivalent to about 5, 10 or 20% amoxicillin. The resulting solution which can also be used for IV or IM administration is then immediately added to sufficient normal saline or 5% aqueous dextrose to form a solution containing the equivalent of about 0.2 to 3% by weight amoxicillin.

Thus, the stable dry powder of amoxicillin trihydrate and anhydrous sodium carbonate is first formed and packaged into vials. When the clinician is ready to administer amoxicillin either intramuscularly or intravenously, the clinician dissolves the powder in sufficient sterile water to provide the desired concentration of amoxicillin and immediately injects the solution into the patient. If a slow prolonged administration is desired, then an intravenous drip is used. The formulation for the intravenous drip is formed by dissolving the powder in sterile water to form a concentrated solution of amoxicillin with the concentration about the same as for IV and IM administration, then immediately mixing the solution with sufficient saline or dextrose solution to achieve the desired concentration of amoxicillin, then administering the solution by IV drip.

Since stability is also a function of concentration, the intravenous drip solutions are quite stable and do not lose more than 10% activity at room temperature within 8 hours for the more dilute solutions or within 4 hours for the more concentrated solutions. The more concentrated IV and IM solutions must be used immediately after preparation, e.g., within 1 hour. This stability is acceptable to the clinician and compares favorably with the stability of the widely used and accepted injectable compositions of sodium ampicillin. The amoxicillin solution when added to the common 0.9% saline or 5% dextrose intravenous drip solution tends to be more stable in the saline solution than the dextrose at equivalent amoxicillin concentrations.

The following Examples illustrate the invention.

EXAMPLE 1

1.15 Grams of amoxicillin trihydrate (85.1% equivalent anhydrous free acid) was blended with 0.4 grams of anhydrous sodium carbonate. This resulted in a powder mixture containing 1.5 moles per mole of amoxicillin free acid. About 5% and 10% solutions of amoxicillin were made by dissolving 1.55 grams of the blended material in 19 and 9 ml. of distilled water respectively. The stability of the solutions was satisfactory for their use in IV or IM administration.

EXAMPLE 2

Amoxicillin trihydrate (84.9% of anhydrous amoxicillin free acid) and anhydrous sodium carbonate powder were blended in 1:1.75 and 1:1.38 molar ratios based on the free acid respectively. Vials were filled with the blended material so that they each contained 0.58 grams of amoxicillin and 0.26 grams or 0.21 grams of $Na_2CO_3$. Solutions containing about 20, 10 or 5% of amoxicillin by weight are produced by adding respectively 2, 4.5 or 9.5 ml. distilled water to each vial. The stability of the solutions was satisfactory for their use in IV or IM administration.

EXAMPLE 3

Sufficient amoxicillin trihydrate and anhydrous sodium carbonate powder were blended to produce powders containing 1.5 and 1.75 moles of $Na_2CO_3$ per mole of anhydrous amoxicillin free acid. Vials were filled with the blended material in sufficient amount to contain 0.65 grams of amoxicillin trihydrate (10% excess) and 0.253 or 0.286 gram $Na_2CO_3$. Solutions containing the equivalent of about 20, 10 or 5% by weight anhydrous amoxicillin free acid were produced by adding 2, 4.5 or 9.5 ml. of distilled water to the vials. The stability of the solutions was satisfactory for their use in IV or IM administration.

EXAMPLE 4

Three vials were each filled with 0.65 grams amoxicillin trihydrate. A second set of three vials were each filled with 0.265 grams anhydrous $Na_2CO_3$ which was dissolved in 2, 4.5 or 9.5 ml. of distilled water. Solutions containing about 20, 10 and 5% by weight amoxicillin were made by adding the sodium carbonate solutions to the amoxicillin containing vials. The resulting solutions were sufficiently stable to be used for IV or IM administration.

EXAMPLE 5

Sufficient amoxicillin trihydrate and anhydrous $Na_2CO_3$ powder were blended to form a powder containing the equivalent of 1.6 moles of $Na_2CO_3$ per mole of amoxicillin. Vials were filled with sufficient amount of the blended material to contain 0.65 grams of amoxicillin trihydrate and 0.265 grams of $Na_2CO_3$. Solutions containing about 20, 10 and 5% by weight equivalent to anhydrous amoxicillin free acid were formed by adding respectively 2, 4.5 or 9.5 ml. of distilled water to the vials. The resulting solutions were sufficiently stable to use in IV or IM administration.

EXAMPLE 6

Ten percent solutions prepared as in Example 5 were added to a sodium chloride solution (normal saline, 9 mg./ml.) to yield concentrations of 0.5 mg./ml., 1.0 mg./ml., 2.0 mg./ml., 30 mg./ml. of amoxicillin. Also about 10% solutions prepared as in Example 5 were added to 5% aqueous dextrose to yield concentrations of 0.5 mg./ml. and 1.0 mg./ml. of amoxicillin. All the solutions were sufficiently stable to be used in intravenous drip administration. The saline solutions had less than 10% loss in potency in 8 hours, the maximum interval over which a drug is usually administered. The dextrose solution had less than 10% loss in four hours, an acceptable stability for such solutions.

We claim:

1. An injectable solution for intramuscular or intravenous administration containing 1.0–2.0 moles of anhydrous sodium carbonate per mole of amoxicillin free acid, said amoxicillin being present in said solution in sufficient amount to provide from about 5% to 20% by weight of amoxicillin.

2. The injectable solution of claim 1 wherein the mole ratio of anhydrous sodium carbonate is 1.38–1.75.

3. The injectable solution of claim 1 wherein the mole ratio of anhydrous sodium carbonate is 1.6.

4. A stable intravenous drip solution containing 1.0 to 2.0 moles of anhydrous sodium carbonate per mole of amoxicillin free acid, said amoxicillin being present in said solution in sufficient amount to provide about 0.2 to 3% by weight amoxicillin.

5. The intravenous drip solution of claim 4 wherein the mole ratio of anhydrous sodium carbonate is 1.38–1.75.

6. The intravenous drip solution of claim 4 wherein the mole ratio of anhydrous sodium carbonate is 1.6.

* * * * *